United States Patent [19]
Allard et al.

[11] Patent Number: 5,882,632
[45] Date of Patent: Mar. 16, 1999

[54] COMPOSITIONS COMPRISING A DIBENZOYLMETHANE DERIVATIVE, A 1,3,5-TRIAZINE DERIVATIVE AND A SILICON DERIVATIVE CONTAINING A BENZALMALONATE FUNCTION, AND METHODS OF USE THEREFOR

[75] Inventors: Delphine Allard, Colombes; Serge Forestier, Claye Souilly, both of France

[73] Assignee: Societe L'Oreal S.A., Paris, France

[21] Appl. No.: 992,475

[22] Filed: Dec. 17, 1997

[30] Foreign Application Priority Data

Dec. 17, 1996 [FR] France .................................. 96 15512

[51] Int. Cl.$^6$ ............................ A61K 7/42; A61K 31/53; A61K 31/12; A61K 7/00

[52] U.S. Cl. .............................. 424/59; 424/60; 424/400; 424/401; 514/242; 514/679

[58] Field of Search ............................ 424/89, 60, 400, 424/401; 514/242, 679

[56] References Cited

FOREIGN PATENT DOCUMENTS

| 0383655 | 8/1990 | European Pat. Off. . |
| 0392882 | 10/1990 | European Pat. Off. . |
| 0517104 | 12/1992 | European Pat. Off. . |
| 0689828 | 1/1996 | European Pat. Off. . |
| 0709080 | 5/1996 | European Pat. Off. . |

*Primary Examiner*—Shelley A. Dodson
*Attorney, Agent, or Firm*—Burns, Doane, Swecker & Mathis, L.L.P.

[57] ABSTRACT

The present invention relates to novel cosmetic and/or dermatological compositions comprising, in a cosmetically and/or dermatologically acceptable support, (i) a dibenzoylmethane derivative, in particular 4-tert-butyl-4'-methoxydibenzoylmethane, (ii) at least one specific 1,3,5-triazine derivative, and (iii) at least one silicone derivative containing a benzalmalonate function. These compositions are particularly photostable.

The invention also relates to the use of these compositions in the cosmetic and/or dermatological fields, in particular, as a sunscreen.

27 Claims, No Drawings

COMPOSITIONS COMPRISING A DIBENZOYLMETHANE DERIVATIVE, A 1,3, 5-TRIAZINE DERIVATIVE AND A SILICON DERIVATIVE CONTAINING A BENZALMALONATE FUNCTION, AND METHODS OF USE THEREFOR

CROSS-REFERENCE TO COMPANION APPLICATIONS

Our copending application Ser. No. 08/992,476 and Ser. No. 08/992,477, both filed concurrently herewith and assigned to the assignee hereof.

BACKGROUND OF THE INVENTION

1. Technical Field of the Invention

The present invention relates to novel cosmetic and/or dermatological compositions (referred to herein below as sunscreen compositions) intended for protecting the skin and/or the hair against the deleterious effects of UV radiation, in particular, solar radiation. More specifically, the invention relates to novel cosmetic and/or dermatological compositions with enhanced photostability and comprising, in a cosmetically and/or dermatologically acceptable support, a combination of at least three specific UV-screening agents.

The invention also relates to the use of photoprotecting compositions in the cosmetic and/or dermatological fields.

2. Description of the Prior Art

It is known to this art that light radiation of wavelengths of from 280 nm to 400 nm promotes tanning of the human epidermis, and that light radiation with wavelengths, more particularly, of from 280 to 320 nm, i.e., UV-B irradiation, causes skin burning and erythema which can impair the development of a natural tan. For these reasons, as well as for aesthetic reasons, there is an increasing demand for means of controlling this natural tanning in order to thereby control the color of the skin. This UV-B radiation must be screened from the skin.

It is also known to this art that UV-A radiation of wavelengths of from 320 to 400 nm, which tan the skin, also adversely affects it, especially in the case of sensitive skin or skin which is continually exposed to solar radiation. UV-A rays especially cause a loss in the elasticity of the skin and the appearance of wrinkles, thereby promoting premature skin aging. Such irradiation promotes triggering of the erythemal reaction or amplifies this reaction in certain individuals. They may even be the cause of phototoxic or photoallergic reactions. Thus, for aesthetic and cosmetic reasons, such as conservation of the natural elasticity of the skin, for example, an ever-increasing number of people wish to control the effect of UV-A rays on their skin, it is therefor desirable also to screen out UV-A radiation.

Thus, with the aim of providing protection for the skin and the hair against UV radiation as a whole, this protection being as full and as effective as possible, combinations of screening agents which are active in the UV-A range and of screening agents which are active in the UV-B range are generally used in the manufacture of antisun compositions.

In this respect, a particularly advantageous family of UV-A screening agents currently include the dibenzoylmethane derivatives and, in particular, 4-tert-butyl-4'-methoxydibenzoylmethane, which effectively have a high intrinsic power of absorption. These dibenzoylmethane derivatives, which are products that are well known in the art as sunscreen agents that are active in the UV-A range, are described in particular in FR-A-2,326,405 and FR-A-2,440, 933, as well as in EP-A-0,114,607. 4-(Tert-butyl)-4'-methoxydibenzoylmethane is currently sold under the trademark "Parsol 17891" by Givaudan.

Similarly, 1,3,5-triazine derivatives and, in particular, 2,4,6-tris[p-(2'-ethylhexyl-1'-oxycarbonyl)anilino]-1,3,5-triazine, sold under the trademark "Uvinul T 150" by BASF, have a high power for absorbing UV-B radiation. It would thus be very advantageous to be able to use those compounds in combination with 4-tert-butyl-4'-methoxydibenzoylmethane for the purpose of obtaining products offering wide and effective protection throughout the full UV radiation range.

However, the inventors have observed that when these 1,3,5-triazine derivatives are in the presence of dibenzoylmethane derivatives, in particular, 4-tert-butyl-4'-methoxydibenzoylmethane, and under UV irradiation, they have the disadvantage of undergoing considerable chemical degradation. Under these conditions, the combination of two screening agents no longer allows broad, prolonged sunscreen protection for the skin and the hair.

SUMMARY OF THE INVENTION

After considerable research conducted in the field of photoprotection, the inventors have unexpectedly and surprisingly discovered that the introduction of a silicone derivative containing a specific benzalmalonate function into a composition containing a dibenzoylmethane derivative, in particular, 4-tert-butyl-4'-methoxydibenzoylmethane, in combination with at least one 1,3,5-triazine derivative and, in particular, with 2,4,6-tris[p-(2'-ethylhexyl-1'-oxycarbonyl)anilino]-1,3,5-triazine, allows the photostability of this 1,3,5,-triazine derivative in the composition, and thus the overall efficacy of the composition, to be enhanced quite substantially.

The subject of the present invention is thus novel cosmetic and/or dermatological compositions comprising, in a cosmetically and/or dermatologically acceptable support or carrier, (i) a dibenzoylmethane derivative, (ii) at least one 1,3,5-triazine derivative corresponding to formula (I) below:

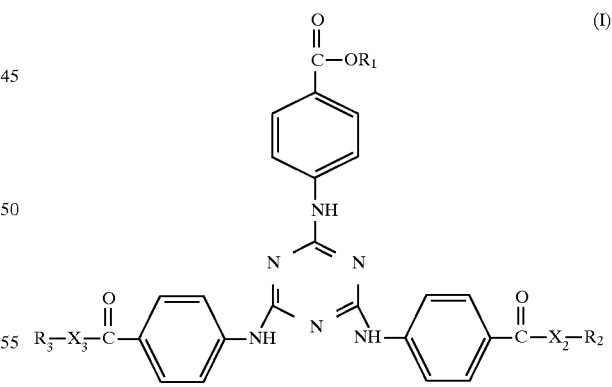

wherein:

$X_2$ and $X_3$, which may be identical or different, represent oxygen or an —NH— radical;

$R_1$, $R_2$ and $R_3$, which may be identical or different, are each a hydrogen; an alkali metal; an ammonium radical optionally substituted with one or more alkyl or hydroxyalkyl radicals; a linear or branched $C_1$–$C_{18}$ alkyl radical; a $C_5$–$C_{12}$ cycloalkyl radical optionally substituted with one or more $C_1$–$C_4$ alkyl radicals; a polyoxyethylenated radical comprising from 1 to 6 ethylene oxide units and whose terminal OH group is methylated; or a radical of formulae (II), (III) or (IV) below:

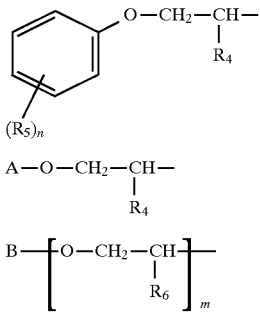

$$A-O-CH_2-CH-R_4 \quad (III)$$

$$B-[O-CH_2-CH(R_6)]_m \quad (IV)$$

wherein:

$R_4$ is hydrogen or a methyl radical;

$R_5$ is a $C_1-C_9$ alkyl radical;

n is an integer ranging from 0 to 3;

m is an integer ranging from 1 to 10;

A is a $C_4-C_8$ alkyl radical or a $C_5-C_8$ cycloalkyl radical;

B is a linear or branched $C_1-C_8$ alkyl radical; a $C_5-C_8$ cycloalkyl radical; or an aryl radical optionally substituted with one or more $C_1-C_4$ alkyl radicals;

$R_6$ is hydrogen or a methyl radical, and (iii) at least one silicon derivative containing a benzalmalonate function comprising at least one unit of formula (V) below:

$$O_{(3-a)/2}Si(R_7)_a-Y-(O)_b-C_6(R_8)_2H_2-CH=C-[C(O)OR_9]_2 \quad (V)$$

wherein:

$R_7$ represents an optionally halogenated $C_1-C_{10}$ alkyl radical or a phenyl radical or a trimethylsilyloxy radical, $R_8$ represents a hydrogen atom, a hydroxyl radical, a $C_1-C_6$ alkyl radical, a $C_1-C_6$ alkoxy radical or a trimethylsilyloxy radical, $R_9$ represents a $C_1-C_8$ alkyl radical, a is an integer chosen between 0 and 3 inclusive, b is equal to 0 or 1, Y represents a divalent radical corresponding to one of formulae (1) to (4) below:

$$\begin{array}{c} -CHR_{10} \\ \parallel \\ [C(R_{10})_2]_p- \end{array} \quad (1)$$

$$-CR_{10}=CH-[C(R_{10})_2]_p- \quad (2)$$

$$\begin{array}{c} -CR_{10}-CH(R_{10})_2 \\ \parallel \\ [C(R_{10})_2]_p- \end{array} \quad (3)$$

$$-C(R_{10})_2-CHR_{10}-[C(R_{10})_2]_p- \quad (4)$$

wherein:

$R_{10}$ represents a hydrogen atom or a $C_1-C_5$ alkyl radical, p is an integer between 1 and 10 inclusive, it being understood that the group $-Y-(O)_b-$ and the two groups $R_8$ are linked to the aromatic ring, without discrimination, in the para position and in the two meta positions relative to the group $-CH=C-[C(O)OR_9]_2$.

Thus, according to the present invention, cosmetic and/or dermatological compositions containing a dibenzoylmethane derivative, in particular, 4-tert-butyl-4'-methoxydibenzoylmethane, in combination with at least one 1,3,5-triazine derivative, can be prepared, wherein the concentration of 1,3,5-triazine derivative in the composition remains relatively constant even if these compositions are exposed to light.

DETAILED DESCRIPTION OF BEST MODE AND SPECIFIC/PREFERRED EMBODIMENTS OF THE INVENTION

The silicone derivatives containing a benzalmalonate function which are used in the practice of the present invention have the advantage of having good intrinsic screening power, which contributes to the protection against UV radiation afforded by the compositions, and, furthermore, the combined screening systems [dibenzoylmethane derivative+1,3,5-triazine derivative+silicone derivative containing a benzalmalonate function] proves to have very good overall stability when exposed to UV radiation (photostability), which is another advantage of the compositions of the present invention.

The present invention features a silicone derivative containing a benzalmalonate function formulated into a cosmetic and/or dermatological composition containing a dibenzoylmethane derivative, in particular, 4-tert-butyl-4'-methoxydibenzoylmethane, in combination with at least one 1,3,5-triazine derivative as defined above, in order to enhance the stability to UV radiation (photostability) of the 1,3,5-triazine derivative in the compositions.

The subject of the present invention is also a process for enhancing the stability of a composition to UV radiation (photostability), and thus the efficacy, of a cosmetic and/or dermatological composition comprising a dibenzoylmethane derivative, in particular, 4-tert-butyl-4'-methoxydibenzoylmethane, and a 1,3,5-triazine derivative as defined above, in particular, 2,4,6-tris[p-(2'-ethylhexyl-1'-oxycarbonyl)anilino]-1,3,5-triazine. The process comprises introducing an effective amount of a silicone derivative containing a benzalmalonate function as defined above into the composition.

By the expression "effective amount of silicon derivative containing a benzalmalonate function" is intended an amount which is sufficient to obtain a noticeable and significant improvement in the photostability of the 1,3,5-triazine derivative(s) contained in the composition. This minimum amount of stabilizer can vary depending on the nature of the cosmetically acceptable support selected for the composition, and can readily be determined by means of a standard test for measuring the photostability, such as that given in the examples below.

Other characteristics, aspects and advantages of the present invention will become apparent on reading the detailed description which follows.

As indicated above, the dibenzoylmethane derivatives which can be used according to the present invention are products that are already well known in the art and are described, in particular, in FR-A-2,326,405, FR-A-2,440,933 and EP-A-114,607 mentioned above. It is, of course, possible to use one or more dibenzoylmethane derivatives in the practice of the present invention.

The dibenzoylmethane derivatives according to the present invention comprise, in particular, in a non-limiting manner:

2-methyldibenzoylmethane, 4-methyldibenzoylmethane, 4-isopropyldibenzoylmethane, 4-tert-butyldibenzoylmethane, 2,4-dimethyldibenzoylmethane,
2,5-dimethyldibenzoylmethane,
4,4'-diisopropyldibenzoylmethane,
4-tert-butyl-4'-methoxydibenzoylmethane,
2-methyl-5-isopropyl-4'-methoxydibenzoylmethane,
2-methyl-5-tert-butyl-4'-methoxydibenzoylmethane,
2,4-dimethyl-4'-methoxydibenzoylmethane,
2,6-dimethyl-4-tert-butyl-4'-methoxydibenzoylmethane,
4,4'-dimethoxydibenzoylmethane.

Among the dibenzoylmethane derivatives, it is preferred to use 4-(tert-butyl)-4'-methoxydibenzoylmethane, in particular, that sold under the trademark "Parsol 1789" by Givaudan. That compound/sunscreen corresponds to the following structural formula:

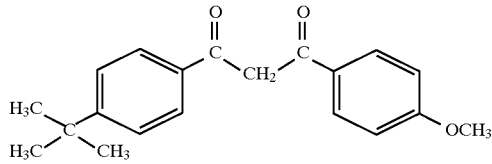

Another preferred dibenzoylmethane derivative is 4-isopropyldibenzoylmethane. This sunscreen is sold under the trademark "Eusolex 8020" by Merck, and corresponds to the following structural formula:

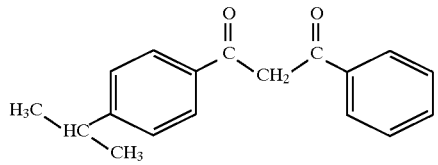

The dibenzoylmethane derivatives can be present in the compositions of the present invention in an amount ranging from 0.2% to 15% by weight, relative to the total weight of the composition. Preferably, the amount ranges from 0.2% to 10%.

A second compound in the compositions envisaged by the present invention is a particular 1,3,5-triazine derivative. Thus, the 1,3,5-triazine derivatives which can be used in the context of the present invention comprise those corresponding to formula (I) below:

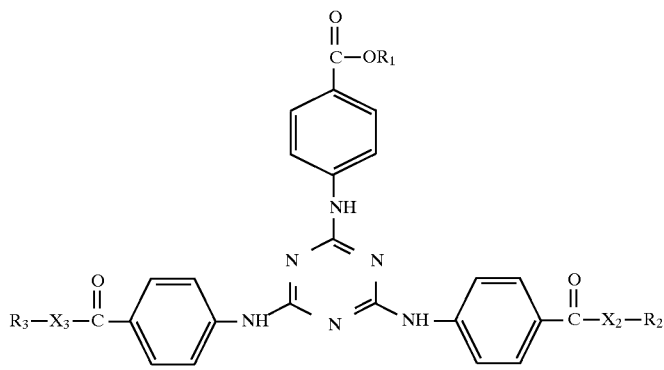

wherein:

$X_2$ and $X_3$, which may be identical or different, represent oxygen or an —NH— radical;

$R_1$, $R_2$ and $R_3$, which may be identical or different, are each a hydrogen; an alkali metal; an ammonium radical optionally substituted with one or more alkyl or hydroxyalkyl radicals; a linear or branched $C_1$–$C_{18}$ alkyl radical; a $C_5$–$C_{12}$ cycloalkyl radical optionally substituted with one or more $C_1$–$C_4$ alkyl radicals; a polyoxyethylenated radical comprising from 1 to 6 ethylene oxide units and whose terminal OH group is methylated; a radical of formulae (II), (III) or (IV):

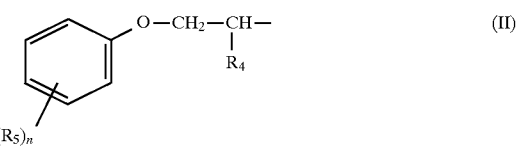

wherein:
$R_4$ is hydrogen or a methyl radical;
$R_5$ is a $C_1$–$C_9$ alkyl radical;
n is an integer ranging from 0 to 3;
m is an integer ranging from 1 to 10;
A is a $C_4$–$C_8$ alkyl radical or a $C_5$–$C_8$ cycloalkyl radical;
B is a linear or branched $C_1$–$C_8$ alkyl radical; a $C_5$–$C_8$ cycloalkyl radical; or an aryl radical optionally substituted with one or more $C_1$–$C_4$ alkyl radicals; and
$R_6$ is hydrogen or a methyl radical.

Obviously, in the above definition, when $X_2$ and/or $X_3$ represent an —NH— radical, then the corresponding radical(s) $R_2$ and/or $R_3$ are other than an alkali metal or an ammonium radical.

The preferred 1,3,5-triazine derivatives are those described, in particular, in EP-A-0,517,104, namely, 1,3,5-triazines corresponding to formula (I) above and having all of the following characteristics:

$X_2$ and $X_3$ are identical and represent oxygen;
$R_1$ is a $C_5$–$C_{12}$ cycloalkyl radical optionally substituted with one or more $C_1$–$C_4$ alkyl radicals; or a radical of formulae (II), (III) or (IV) above wherein:
B is a $C_1$–$C_4$ alkyl radical; and
$R_6$ is a methyl radical;
$R_2$ and $R_3$, which may be identical or different, are each a hydrogen; an alkali metal; an ammonium radical optionally substituted with one or more alkyl or hydroxyalkyl radicals; a linear or branched $C_1$–$C_{18}$ alkyl radical; a $C_5$–$C_{12}$ cycloalkyl radical optionally substituted with one or more $C_1$–$C_4$ alkyl radicals; or a radical of formulae (II), (III) or (IV) above wherein:

B is a $C_1$–$C_4$ alkyl radical; and $R_6$ is a methyl radical.

A second preferred set of 1,3,5-triazine derivatives according to the invention are those described, in particular, in EP-A-570,838, namely, 1,3,5-triazines corresponding to formula (I) and having all of the following characteristics:

$X_3$ is an —NH— radical;

$R_3$ is a linear or branched $C_1$–$C_{18}$ alkyl radical; or a $C_5$–$C_{12}$ cycloalkyl radical optionally substituted with one or more $C_1$–$C_4$ alkyl radicals;

$R_1$ is hydrogen; an alkali metal; an ammonium radical; a radical of formula (IV); a linear or branched $C_1$–$C_{18}$ alkyl radical; or a $C_5$–$C_{12}$ cycloalkyl radical optionally substituted with one or more $C_1$–$C_4$ alkyl radicals;

if $X_2$ is an —NH— radical, then $R_2$ is a linear or branched $C_1$–$C_{18}$ alkyl radical; or a $C_5$–$C_{12}$ cycloalkyl radical optionally substituted with one or more $C_1$–$C_4$ alkyl radicals;

if $X_2$ is oxygen, then $R_2$ is hydrogen; an alkali metal; an ammonium radical; a radical of formula (IV); a linear or branched $C_1$–$C_{18}$ alkyl radical; or a $C_5$–$C_{12}$ cycloalkyl radical optionally substituted with one or more $C_1$–$C_4$ alkyl radicals.

A particularly preferred 1,3,5-triazine of the second preferred set of compounds is that corresponding to the following formula:

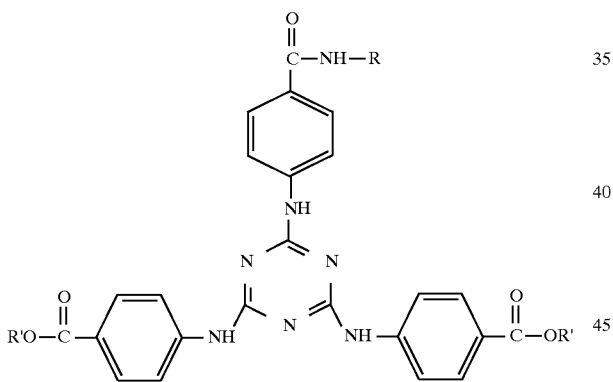

wherein R' represents a 2-ethylhexyl radical and R represent a tert-butyl radical.

A third preferred set of compounds is that described, in particular, in U.S. Pat. No. 4,724,137, namely, 1,3,5-triazines corresponding to formula (I) and having the following characteristics:

$X_2$ and $X_3$ are identical and represent oxygen;

$R_1$, $R_2$ and $R_3$ are identical and represent a $C_6$–$C_{12}$ alkyl radical or a polyoxyethylenated radical comprising from 1 to 6 ethylene oxide units and in which the terminal OH group is methylated.

A particularly preferred 1,3,5-triazine of this third preferred set is 2,4,6-tris[p-(2'-ethylhexyl-1'-oxycarbonyl) anilino]-1,3,5-triazine, which is a sunscreen which is known in the art. It is active in the UV-B range, is in solid form and is sold, in particular, under the trademark "Uvinul T 150" by BASF. This compound corresponds to the following formula:

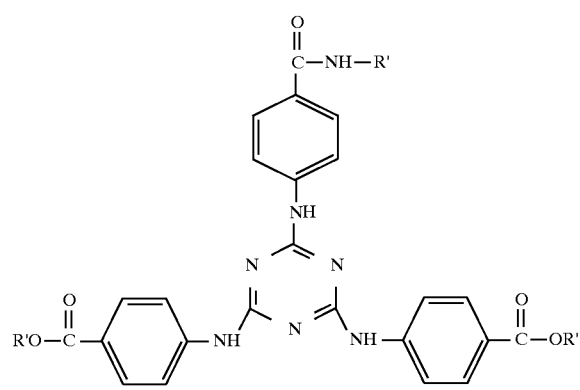

wherein R' represents a 2-ethyl(hexyl radical.

The 1,3,5-triazine derivatives) is/are generally present in the compositions of the present invention in a proportion which may range from 0.5% to 20%, preferably from 1% to 10%, by weight, relative to the total weight of the composition.

A third essential compound of the compositions according to the invention is a silicone derivative containing a benzalmalonate function. Preferably, the silicone derivatives containing a benzalmalonate function which can be used in the present invention are diorganosiloxanes or silanes which comprise at least one unit of formula (V) below: wherein:

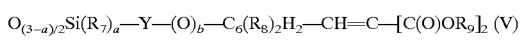

$R_7$ represents an optionally halogenated $C_1$–$C_{10}$ alkyl radical or a phenyl radical or a trimethylsilyloxy radical, $R_8$ represents a hydrogen atom, a hydroxyl radical, a $C_1$–$C_6$ alkyl radical, a $C_1$–$C_6$ alkoxy radical or a trimethylsilyloxy radical, $R_9$ represents a $C_1$–$C_8$ alkyl radical, a is an integer ranging from 0 to 3, inclusive, b is equal to 0 or 1, Y represents a divalent radical corresponding to one of formulae (1) to (4) below:

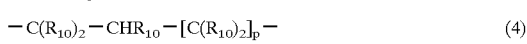

wherein:

$R_{10}$ represents a hydrogen atom or a $C_1$–$C_5$ alkyl radical, p is an integer ranging from 1 to 10, inclusive, it being understood that the group —Y—(O)$_b$— and the two groups $R_8$ are linked to the aromatic ring, without discrimination, in the para position and in the two meta positions relative to the group —CH=C—[C(O)OR$_9$]$_2$.

In formula (V), when A is other than 3, the silicone derivatives containing a benzalmalonate function which can be used according to the present invention are diorganosiloxanes which can also comprise at least one unit of general formula (VI):

$$(R_{11})_c SiO_{(4-c)/2} \quad (VI)$$

wherein:

$R_{11}$ represents a hydrogen atom or an optionally halogenated $C_1$–$C_{10}$ hydrocarbon radical, c is an integer ranging from 0 to 3, inclusive.

The diorganosiloxanes containing a benzalmalonate function are described, along with processes for their preparation, in EP-A-358,584, EP-A-392,882, EP-A-538,431 and EP-A-709,080.

A particularly preferred set of diorganosiloxanes is that defined by the diorganosiloxanes containing a benzalmalonate function, corresponding to either formulae (5) or (6) below:

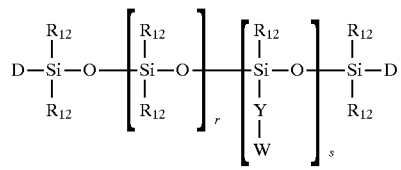

(5)

or

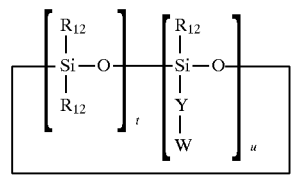

(6)

wherein:

$R_{12}$, each of which may be identical or different, is independently $C_1$–$C_{10}$ alkyl, phenyl or 3,3,3-trifluoropropyl radicals, wherein at least 80%, in numerical terms, of the radicals $R_{12}$ are methyl, D, which may be identical or different, is independently the same as the radicals for $R_{12}$ above or the radical Y—W, r is an integer ranging from 0 to 200, inclusive, and s is an integer ranging from 0 to 50, inclusive, and if s=0, at least one of the two symbols D denotes Y—W, u is an integer ranging from 1 to 20, inclusive, and t is an integer ranging from 0 to 20, inclusive, wherein t+u is equal to or greater than 3, Y has the same definition as in formula (V) above, W represents the radical

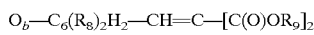

wherein $R_8$, $R_9$ and B have the same definitions as in formula (V) above.

In this set, particularly preferred are the linear, random or block polymers of formula (5) having at least one of the following characteristics:

$R_{12}$ is methyl,

D is methyl, $R_8$ is hydrogen or O—$CH_3$, $R_9$ is ethyl or 2-ethylhexyl, r is between 0 and 20, inclusive, and s is between 1 and 15, inclusive.

A particularly preferred diorganosiloxane of this set is the compound (referred to herein below as compound (cl)) of formula (5), which has all of the following characteristics:

$R_{12}$ is methyl,

D is methyl, r=s=5, and Y—W represents:

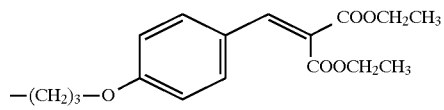

In a particularly preferred embodiment of the present invention, a sat of compounds which is particularly desired is that defined by the diorganosiloxanes containing a benzalmalonate function corresponding to formula (5) above wherein:

$R_{12}$ is methyl, $0 \leq r \leq 130$ and $0 \leq s \leq 20$,

D is methyl or Y—W,

Y—W represents:

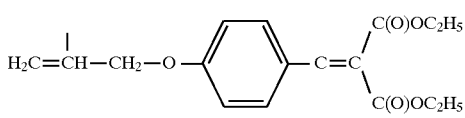

or

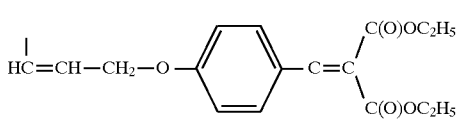

with the proviso that:

when D is Y—W, then s=0, and when D is methyl, then $1 \leq s \leq 20$, and mixtures thereof.

A particularly preferred compound of this latter family is poly dimethyl/methyl (3-(4-2,2-bisethoxycarbonylvinyl) phenoxy)propenyl)siloxane sold under the trademark "Parsol SLX" by Givaudan.

Thus, when a sufficient amount of a silicone derivative containing a benzalmalonate function as defined above is added to a sunscreen composition containing a dibenzoylmethane derivative, in particular, 4-tert-butyl-4'-methoxydibenzoylmethane, and a 1,3,5-triazine derivative as defined above, an increase in the stability of the 1,3,5-triazine derivative to light is observed, and thus an increase in the efficacy of the sunscreen composition over time.

Preferably, the silicon derivative containing a benzalmalonate function is present in the compositions according to the invention in a proportion at least equal to 0.5% by weight relative to the total weight of the composition. More preferably, this proportion ranges from 0.5% to 20% by weight relative to the total weight of the composition.

The cosmetic and/or dermatological compositions disclosed by the present invention can, of course, contain one or more additional hydrophilic or lipophilic U-VA- and/or UV-B-active sunscreens (absorbers) other than, of course, the three sunscreen compounds identified above. These additional sunscreen agents are advantageously selected, in particular, from among the cinnamic derivatives, salicylic derivatives, benzylidene camphor derivatives, benzimidazole derivatives, triazine derivatives other than those mentioned above, benzophenone derivatives, β,β'-diphenylacrylate derivatives, p-aminobenzoic acid derivatives, and the screening polymers and screening silicones described in WO-93/04665. Other examples of organic sunscreen agents are provided in EP-A-487,404.

The compositions according to the invention can also contain agents for the artificial tanning and/or bronzing of the skin (self-tanning agents), such as, for example, dihydroxyacetone (DHA).

The cosmetic and/or dermatological compositions according to the present invention can also contain pigments or nanopigments (average size of the primary particles: generally range from 5 nm to 100 nm, preferably from 10 to 50 nm) of coated or uncoated metal oxides such as, for example, nanopigments of titanium dioxide (amorphous or crystallized in rutile and/or anatase form), iron oxide, zinc oxide, zirconium oxide or cerium oxide, which are all photoprotective agents which are well known to this art and act by physically blocking (reflection and/or diffusion) UV radiation. Standard coating agents are alumina and/or aluminum stearate. Such coated or uncoated metal oxide nanopigments are described, in particular, in EP-A-518,772 and EP-A-518,773.

The compositions in accordance with the present invention may comprise typical additives and adjuvants in the cosmetics field, such as fatty substances, organic solvents, ionic or nonionic thickeners, softeners, antioxidants, anti-free-radical agents, opacifiers, stabilizers, emollients, silicones, α-hydroxy acids, antifoaming agents, moisturizers, vitamins, fragrances, preservatives, surfactants, fillers, sequestering agents, polymers, propellants, basifying or acidifying agents, dyes or any other ingredients usually used in the cosmetic and/or dermatological field, in particular, for the formulation of sunscreen compositions in the form of emulsions.

Exemplary fatty substances include an oil or a wax or mixtures thereof. By the term "oil" is intended a compound which is liquid at room temperature. The term wax is intended to mean a compound which is solid or substantially solid at room temperature, and whose melting point is generally above 35° C.

Exemplary oils, include mineral oils (petroleum jelly); plant oils (sweet almond oil, macadamia oil, grapeseed oil, jojoba oil); synthetic oils such as perhydrosqualene, fatty alcohols, fatty acids or fatty esters (such as C12–C15 alkyl benzoates sold under the trademark "Finsolv TN" by Finetex, octyl palmitate, isopropyl lanolate, triglycerides including those of capric/caprylic acid), oxyethylenated or oxypropylenated fatty esters and fatty ethers; silicone oils (cyclomethicone, polydimethylsiloxanes, or PDMS) or fluoro oils; polyalkylenes.

Exemplary waxy compounds include paraffin, carnauba wax, beeswax and hydrogenated castor oil.

Exemplary organic solvents include lower alcohols and polyols.

The thickeners comprise crosslinked polyacrylic acids and modified or unmodified guar gums and celluloses, such as hydroxypropyl guar gum, methylhydroxyethylcellulose and hydroxypropylmethylcellulose.

Needless to say, a person skilled in the art will take care to select the optional additional compound(s) mentioned above (in particular the additional sunscreen agents) and/or the amounts thereof, such that the advantageous properties intrinsically associated with the ternary combination in accordance with the present invention are not, or are not substantially, adversely affected by the additional compounds which may be present.

The compositions according to the invention can be prepared according to techniques which are well known to those skilled in the art, in particular, those intended for the preparation of oil-in-water or water-in-oil type emulsions. The composition of the present invention can be, in particular, in the form of a simple or complex emulsion (O/W, W/O, O/W/O or W/O/W) such as a cream, a milk, or in the form of a gel or a cream gel, a powder or a solid stick and can optionally be packaged as an aerosol or in the form of a foam or a spray.

Preferably, the compositions according to the invention are in the form of an oil-in-water emulsion.

The aqueous phase of this emulsion can comprise a nonionic vesicle dispersion prepared according to known processes (Bangham, Standish and Watkins, *J. Mol. Biol.*, 13, 238 (1965), FR 2,315,991 and FR 2,416,008).

The cosmetic and/or dermatological composition of the present invention can be used as a composition for protecting the human epidermis or the hair against ultraviolet rays, as a sunscreen composition or as a makeup product.

When the cosmetic composition according to the present invention is used to protect the human epidermis against UV rays, or as a sunscreen, it can be in the form of a suspension or a dispersion in solvents or fatty substances, in the form of a nonionic vesicle dispersion or alternatively in the form of an emulsion, preferably an oil-in-water emulsion, such as a cream or a milk, or in the form of ointments, gels, cream gels, solid pencils, sticks, aerosol foams or sprays.

When the cosmetic compositions according to the present invention are used for protecting the hair, they may be in the form of a shampoo, a lotion, a gel, an emulsion, a nonionic vesicle dispersion or a lacquer for the hair and can constitute, for example, a composition which is applied to the hair and rinsed out with water, also referred to as a rinse, to be applied before or after shampooing, before or after dyeing or bleaching, before, during or after permanent-waving or straightening of the hair, a styling or treating lotion or gel, a blow-drying or hairsetting lotion or gel, or a permanent-waving, straightening, dyeing or bleaching composition for the hair.

When the compositions are formulated as a makeup product for the eyelashes, the eyebrows or the skin, such as epidermal treatment creams, foundations, tubes of lipstick, eyeshadows, blushers, mascaras or eyeliners, they may be in solid or pasty, anhydrous or aqueous form, such as oil-in-water or water-in-oil emulsions, nonionic vesicular dispersions or suspensions.

As a guide for the sunscreen formulations having an oil-in-water emulsion support, the aqueous phase (comprising in particular the hydrophilic screening agents) generally represents from 50 to 95% by weight, preferably from 70 to 90% by weight, relative to the formulation as a whole, the oil phase (comprising in particular the lipophilic screening agents) represents from 5 to 50% by weight, preferably from 10 to 30% by weight, relative to the formulation as a whole, and the (co)emulsifier(s) represent(s) from 0.5 to 20% by weight, preferably from 2 to 10% by weight, relative to the formulation as a whole.

In order to further illustrate the present invention and the advantages thereof, the following specific examples are given, is being understood that same are intended only as illustrative and in nowise limitative.

EXAMPLE

Five oil-in-water emulsions A, B, C, D and E were prepared, in which the common support or base has the following composition (the amounts are expressed as a % by weight relative to the total weight of the composition):

| | |
|---|---|
| 80/20 mixture of cetylstearyl alcohol and oxyethylenated cetylstearyl alcohol (33 EO), | 7% |

-continued

| | |
|---|---|
| sold under the trademark "Dehsconet 390" by Tensia | |
| mixture of glyceryl mono- and distearate sold under the trademark "Cerasynth SD" by ISP | 2% |
| cetyl alcohol | 1.5% |
| polydimethylsiloxane sold under the trademark "DC 200 Fluid" by Dow Corning | 1.5% |
| C12/C15 alkyl benzoate sold under the trade name "Finsolv TN" by Finetex | 15% |
| ethylenediaminetetraacetic acid, disodium salt, 2H$_2$O | 0.1% |
| glycerol | 20% |
| preserving agents | qs |
| demineralized water | qs 100% |

Emulsion A (comparative) also comprises a 1,3,5-triazine derivative, which is 2,4,6-tris[p-(2'-ethylhexyl-1'-oxycarbonyl)anilino]-1,3,5-triazine (Uvinul T 150). Emulsion B, which is also comparative, contains Uvinul T 150 in combination with 4-tert-butyl-4'-methoxydibenzoylmethane (Parsol 1789). Emulsion C, according to the invention, comprises, in addition to Uvinul T 150 and Parsol 1789, the above compound referred to as ($c_1$). Emulsion D, which is also according to the invention, comprises, in addition to Uvinul T 150 and Parsol 1789, poly dimethyl/methyl (3-4-2,2-bisethoxycarbonylvinyl)phenoxy)-propenyl)siloxane sold under the trademark "Parsol SLX" by Givaudan. The comparative emulsion E itself comprises Uvinul T 150 in combination with Parsol 1789, but with a standard UV-B sunscreen which is octyl methoxycinnamate, sold under the trademark "Parsol MCX" by Givaudan.

The compositions of emulsions A, B, C, D and E identifying the various sunscreen agents mentioned above are collated in Table (I) below (the amounts are expressed as a % by weight relative to the total weight of the composition):

TABLE (I)

| Screening agent | A comparative | B comparative | C invention | D invention | E comparative |
|---|---|---|---|---|---|
| Uvinul T 150 | 1.5% | 1.5% | 1.5% | 1.5% | 1.5% |
| Parsol 1789 | — | 0.5% | 0.5% | 0.5% | 0.5% |
| Compound $c_1$ | — | — | 10% | — | — |
| Parsol SLX | — | — | — | 10% | — |
| Parsol MCX | — | — | — | — | 10% |

For each of these emulsions, the percentage of residual 2,4,6-tris[p-(2'-ethylhexyl-1'-oxycarbonyl)anilino]-1,3,5-triazine after UV irradiation was determined according to the following procedure: for each formula, four control samples and four test samples were prepared. Next, 16 mg of formula were placed on frosted PMMA (polymethyl methacrylate) plates, which had been prerinsed with water and then dried, and the formula was spread over an area of 2 cm×4 cm. The plates were then irradiated (Suntest CPS Heraeus) for 4 hours in a chamber whose temperature is adjusted to about 35°–40° C. in order to simulate natural UV irradiation, while storing the control plates in darkness during the irradiation time of the other plates.

The samples were then analyzed in the following manner: the screening agents were extracted by immersing each plate in 55 ml of ethanol in order to dissolve the screening agents. The plates and the solvent containing the screening agents were then treated with ultrasound for 5 minutes in order to ensure efficient extraction. The solutions obtained are analyzed by high performance liquid chromatography.

For each formula tested, the level of residual 2,4,6-tris[p-(2'-ethylhexyl-1'-oxycarbonyl)anilino]-1,3,5-triazine after irradiation is given by the ratio of its concentration in the irradiated sample to its concentration in the non-irradiated sample.

The results, as a percentage of remaining 2,4,6-tris[p-(2'-ethylhexyl-1'-oxycarbonyl)anilino]-1,3,5-triazine, are collated in Table (II) below:

TABLE (II)

| Emulsion | Residual Uvinul T 150 |
|---|---|
| Emulsion A (comparative) | 79% |
| Emulsion B (comparative) | 63% |
| Emulsion C (invention) | 100% |
| Emulsion D (invention) | 91% |
| Emulsion E (comparative) | 77% |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A photoprotective cosmetic composition suited for photoprotecting the skin and/or hair against the deleterious effects of UV radiation, comprising an effective UV-screening amount of: (i) a dibenzoylmethane derivative, (ii) at least one 1,3,5-triazine derivative corresponding to formula (I) below:

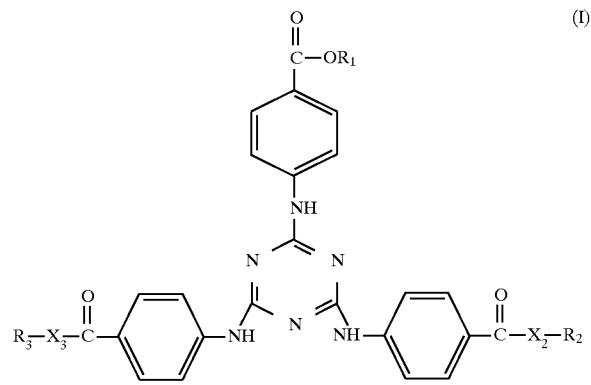

wherein:

$X_2$ and $X_3$, which may be identical or different, represent oxygen or an —NH— radical;

$R_1$, $R_2$ and $R_3$, which may be identical or different, are each hydrogen; an alkali metal; an ammonium radical optionally substituted with one or more alkyl or hydroxyalkyl radicals; a linear or branched $C_1$–$C_{18}$ alkyl radical; a $C_5$–$C_{12}$ cycloalkyl radical optionally substituted with one or more $C_1$–$C_4$ alkyl radicals; a polyoxyethylenated radical comprising from 1 to 6 ethylene oxide units and whose terminal OH group is methylated; or a radical of formulae (II), (III) or (IV) below:

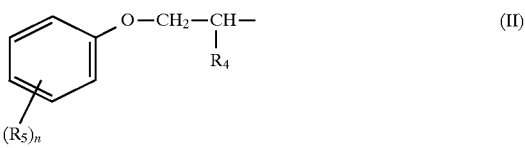

-continued $$A-O-CH_2-CH- \atop | \atop R_4 \qquad (III)$$

$$B-\left[O-CH_2-CH- \atop | \atop R_6\right]_m \qquad (IV)$$

wherein:

$R_4$ is hydrogen or a methyl radical;

$R_5$ is a $C_1$–$C_9$ alkyl radical;

n is an integer ranging from 0 to 3;

m is an integer ranging from 1 to 10;

A is a $C_4$–$C_8$ alkyl radical or a $C_5$–$C_8$ cycloalkyl radical;

B is a linear or branched $C_1$–$C_8$ alkyl radical; a $C_5$–$C_8$ cycloalkyl radical; or an aryl radical optionally substituted with one or more $C_1$–$C_4$ alkyl radicals;

$R_6$ is hydrogen or a methyl radical, and (iii) at least one silicone derivative containing a benzalmalonate function comprising at least one unit of formula (V) below:

$$O_{(3-a)/2}Si(R_7)_a-Y-(O)_b-C_6(R_8)_2H_2-CH=C-[C(O)OR_9]_2 \quad (V)$$

wherein:

$R_7$ represents an optionally halogenated $C_1$–$C_{10}$ alkyl radical or a phenyl radical or a trimethylsilyloxy radical, $R_8$ represents a hydrogen atom, a hydroxyl radical, a $C_1$–$C_6$ alkyl radical, a $C_1$–$C_6$ alkoxy radical or a trimethylsilyloxy radical, $R_9$ represents a $C_1$–$C_8$ alkyl radical, a is an integer ranging from 0 to 3, inclusive, b is equal to 0 or 1, Y represents a divalent radical corresponding to one of formulae (1) to (4):

$$-CHR_{10} \atop \| \atop [C(R_{10})_2]_p- \qquad (1)$$

$$-CR_{10}=CH-[C(R_{10})_2]_p- \qquad (2)$$

$$-CR_{10}-CH(R_{10})_2 \atop \| \atop [C(R_{10})_2]_p- \qquad (3)$$

$$-C(R_{10})_2-CHR_{10}-[C(R_{10})_2]_p- \qquad (4)$$

wherein:

$R_{10}$ represents a hydrogen atom or a $C_1$–$C_5$ alkyl radical, p is an integer ranging from 1 to 10, inclusive, it being understood that the group $-Y-(O)_b-$ and the two groups $R_8$ are linked to the aromatic ring, without discrimination, in the para position and in the two meta positions relative to the group $-CH=C-[C(O)OR_9]_2$.

2. The photoprotective composition as defined by claim 1, wherein the 1,3,5-triazine derivative of formula (I) has the following substituents:

$X_2$ and $X_3$ are identical and represent oxygen;

$R_1$ is a $C_5$–$C_{12}$ cycloalkyl radical optionally substituted with one or more $C_1$–$C_4$ alkyl radicals; or a radical of formulae (II), (III) or (IV) wherein:

B is a $C_1$–$C_4$ alkyl radical; and $R_6$ is a methyl radical;

$R_2$ and $R_3$, which may be identical or different, are each hydrogen; an alkali metal; an ammonium radical optionally substituted with one or more alkyl or hydroxyalkyl radicals; a linear or branched $C_1$–$C_{18}$ alkyl radical; a $C_5$–$C_{12}$ cycloalkyl radical optionally substituted with one or more $C_1$–$C_4$ alkyl radicals; or a radical of formulae (II), (III) or (IV) in which:

B is a $C_1$–$C_4$ alkyl radical; and $R_6$ is a methyl radical.

3. The photoprotective composition as defined by claim 1, wherein the 1,3,5-triazine derivative of formula (I) has the following substituents:

$X_2$ and $X_3$ are identical and represent the —NH— radical;

$R_3$ is a linear or branched $C_1$–$C_{18}$ alkyl radical; or a $C_5$–$C_{12}$ cycloalkyl radical optionally substituted with one or more $C_1$–$C_4$ alkyl radicals;

$R_1$ is hydrogen; an alkali metal; an ammonium radical; a radical of formula (IV); a linear or branched $C_1$–$C_{18}$ alkyl radical; or a $C_5$–$C_{12}$ cycloalkyl radical optionally substituted with one or more $C_1$–$C_4$ alkyl radicals; and $R_2$ is a linear or branched $C_1$–$C_{18}$ alkyl radical; or a $C_5$–$C_{12}$ cycloalkyl radical optionally substituted with one or more $C_1$–$C_4$ alkyl radicals.

4. The photoprotective composition as defined by claim 1, wherein the 1,3,5-triazine derivative of formula (I) has the following substituents:

$X_2$ is oxygen;

$X_3$ is the —NH— radical;

$R_3$ is a linear or branched $C_1$–$C_{18}$ alkyl radical; or a $C_5$–$C_{12}$ cycloalkyl radical optionally substituted with one or more $C_1$–$C_4$ alkyl radicals;

$R_1$ is hydrogen; an alkali metal; an ammonium radical; a radical of formula (IV); a linear or branched $C_1$–$C_{18}$ alkyl radical; or a $C_5$–$C_{12}$ cycloalkyl radical optionally substituted with one or more $C_1$–$C_4$ alkyl radicals; and $R_2$ is hydrogen; an alkali metal; an ammonium radical; a radical of formula (IV); a linear or branched $C_1$–$C_{18}$ alkyl radical; or a $C_5$–$C_{12}$ cycloalkyl radical optionally substituted with one or more $C_1$–$C_4$ alkyl radicals.

5. The photoprotective composition as defined by claim 4, wherein the 1,3,5-triazine derivative corresponds to the following formula:

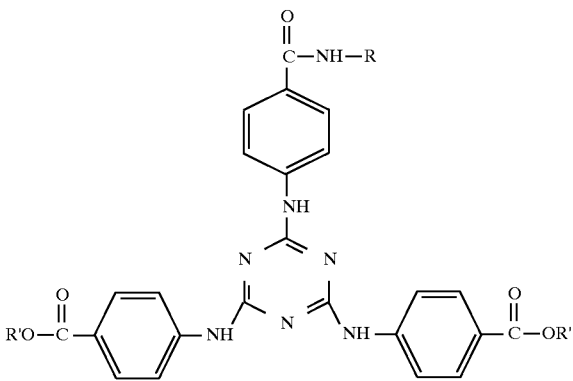

wherein R' represents a 2-ethylhexyl radical and R represents a tert-butyl radical.

6. The photoprotective composition as defined by claim 1, wherein the 1,3,5-triazine derivative has the following substituents:

$X_2$ and $X_3$ are identical and represent oxygen; and $R_1$, $R_2$ and $R_3$ are identical and represent a $C_6$–$C_{12}$ alkyl radical or a polyoxyethylenated radical comprising from 1 to 6 ethylene oxide units and in which the terminal OH is methylated.

7. The photoprotective composition as defined by claim 6, wherein the 1,3,5-triazine derivative corresponds to the following formula:

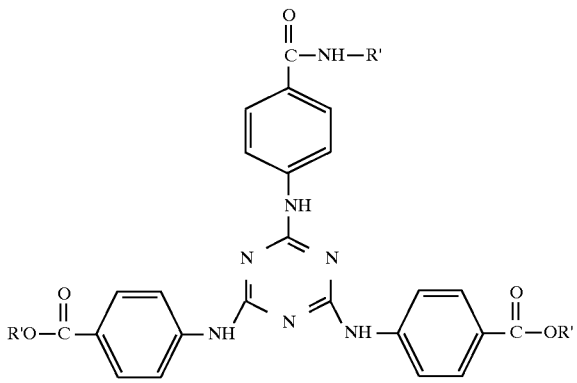

wherein R' represents a 2-ethylhexyl radical.

8. The photoprotective composition as defined by claim 1, wherein the 1,3,5-triazine derivative is present in the composition in an amount ranging from 0.5% to 20% by weight, relative to the total weight of the composition.

9. The photoprotective composition as defined by claim 8, wherein the 1,3,5-triazine derivative is present in the composition in an amount ranging from 1% to 10% by weight, relative to the total weight of the composition.

10. The photoprotective composition as defined by claim 1, wherein the silicone derivative containing a benzalmalonate function comprises at least one unit of formula (V) in which A is other than 3.

11. The photoprotective composition as defined by claim 10, wherein the silicone derivative containing a benzalmalonate function also comprises at least one unit of general formula (VI) below:

  (VI)

wherein:

$R_{11}$ represents a hydrogen atom or an optionally halogenated $C_1$–$C_{10}$ hydrocarbon radical, and c is an integer ranging from 0 to 3, inclusive.

12. The photoprotective composition as defined by claim 11, wherein the silicon derivative containing a benzalmalonate function corresponds to either of the formulae (5) or (6):

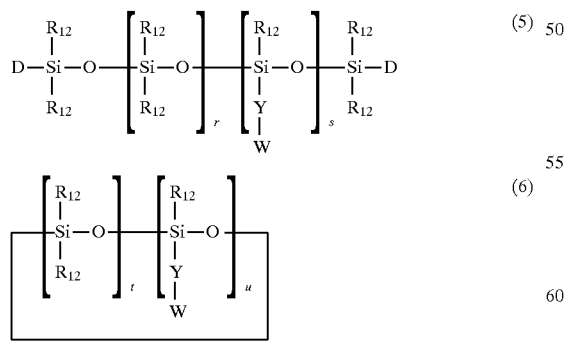

wherein:

$R_{12}$, which may be identical or different, are each a $C_1$–$C_{10}$ alkyl, phenyl or 3,3,3-trifluoropropyl radical, wherein at least 80%, in numerical terms, of the radicals $R_{12}$ are methyl, D, which may be identical or different, are each the same as the radical $R_{12}$ or the radical Y—W, r is an integer ranging from 0 to 200, inclusive, and s is an integer ranging from 0 to 50, inclusive, and if s=0, at least one of the two symbols D denotes Y—W, u is an integer ranging from 1 to 20, inclusive, and t is an integer ranging from 0 to 20, inclusive, it being understood that t+u is equal to or greater than 3, Y has the same meaning as set forth in formula (V), W represents the radical

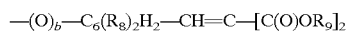

wherein $R_8$, $R_9$ and b have the same meanings as set forth in formula (V).

13. The photoprotective composition as defined by claim 12, wherein the silicone derivative containing a benzalmalonate function is formula (5) and has at least one of the following substituents:

$R_{12}$ is methyl,

D is methyl, $R_8$ is hydrogen or O—$CH_3$, $R_9$ is ethyl or 2-ethylhexyl, r ranges from 0 to 20, inclusive, and s ranges from 1 to 15, inclusive.

14. The photoprotective composition as defined by claim 12, wherein the silicone derivative containing a benzalmalonate function is the compound of formula (5) which has all of the following substituents:

$R_{12}$ is methyl,

D is methyl, r=s=5, and Y—W represents:

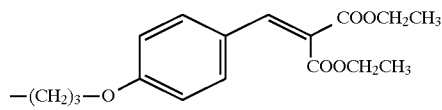

15. The photoprotective composition as defined by claim 12, wherein the silicone derivative containing a benzalmalonate function corresponds to formula (5) wherein:

$R_{12}$ is methyl, $0 \leq r \leq 130$ and $0 \leq s \leq 20$,

D is methyl or Y—W,

Y—W represents:

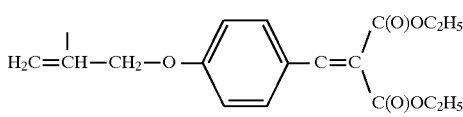

or

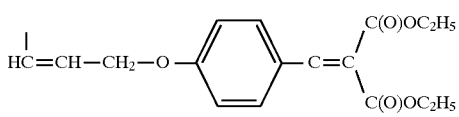

with the proviso that:

when D is Y—W, then s=0, and when D is methyl, then $1 \leq s \leq 20$, and mixtures thereof.

16. The photoprotective composition as defined by claim 15, wherein the silicone derivative containing a benzalmalonate function is poly dimethyl/methyl (3-(4-2,2-bisethoxycarbonylvinyl)phenoxy)propenyl)-siloxane.

17. The photoprotective composition as defined by claim 1, wherein the silicone derivative containing a benzalmalonate function is present in the composition in a proportion at least equal to 0.5% by weight, relative to the total weight of the composition.

18. The photoprotective composition as defined by claim 17, wherein the silicone derivative is from 0.5% to 20% by weight relative to the total weight of the composition.

19. The photoprotective composition as defined by claim 1, wherein the dibenzoylmethane derivative is:

2-methyldibenzoylmethane,
4-methyldibenzoylmethane,
4-isopropyldibenzoylmethane,
4-tert-butyldibenzoylmethane,
2,4-dimethyldibenzoylmethane,
2,5-dimethyldibenzoylmethane,
4,4'-diisopropyldibenzoylmethane,
4-tert-butyl-4'-methoxydibenzoylmethane,
2-methyl-5-isopropyl-4'-methoxydibenzoylmethane,
2-methyl-5-tert-butyl-4'-methoxydibenzoylmethane,
2,4-dimethyl-4'-methoxydibenzoylmethane,
2,6-dimethyl-4-tert-butyl-4'-methoxydibenzoylmethane, or
4,4'-dimethoxydibenzoylmethane.

20. The photoprotective composition as defined by claim 1, wherein dibenzoylmethane derivative is 4-tert-butyl-4'-methoxydibenzoylmethane.

21. The photoprotective composition as defined by claim 1, wherein the dibenzoylmethane derivative is present in the composition in a proportion ranging from 0.2% to 15% by weight, relative to the total weight of the composition.

22. The photoprotective composition as defined by claim 21, wherein the dibenzoylmethane derivative is from 0.2% to 10% by weight, relative to the total weight of the composition.

23. The photoprotective composition as defined by claim 1, wherein said composition is in the form of an oil-in-water emulsion.

24. A UV-protecting shape or article containing an effective UV-protecting amount of the composition as defined by claim 1.

25. A method for photoprotecting human skin and/or hair against the deleterious effects of UV irradiation, comprising topically applying thereto an effective UV-screening amount of the photoprotective composition as defined by claim 1, to a patient in need thereof.

26. A method for controlling variation in skin color promoted by UV irradiation, comprising topically applying thereto an effective UV-screening amount of the composition as defined by claim 1, to a patient in need thereof.

27. A process for enhancing the stability to UV-irradiation of a photoprotective composition comprising a dibenzoylmethane derivative and a 1,3,5-triazine derivative, said process comprising introducing into said composition a stabilizing effective amount of an amide compound.

* * * * *